United States Patent
Sjöstedt

(10) Patent No.: US 8,574,241 B2
(45) Date of Patent: Nov. 5, 2013

(54) STEERABLE STYLET FOR AN IMPLANTABLE MEDICAL LEAD, AND METHOD FOR MANUFACTURE THEREOF

(75) Inventor: Johan Sjöstedt, Hässelby (SE)

(73) Assignee: St. Jude Medical AB, Jarfalla (SE)

( * ) Notice: Subject to any disclaimer, the term of this patent is extended or adjusted under 35 U.S.C. 154(b) by 1175 days.

(21) Appl. No.: 12/302,159

(22) PCT Filed: May 31, 2006

(86) PCT No.: PCT/SE2006/000647
§ 371 (c)(1),
(2), (4) Date: Apr. 21, 2009

(87) PCT Pub. No.: WO2007/139457
PCT Pub. Date: Dec. 6, 2007

(65) Prior Publication Data
US 2009/0248035 A1    Oct. 1, 2009

(51) Int. Cl.
*A61B 19/00*    (2006.01)

(52) U.S. Cl.
USPC .............................................. 606/129

(58) Field of Classification Search
USPC .............................................. 606/129
See application file for complete search history.

(56) References Cited

U.S. PATENT DOCUMENTS

| 5,322,064 A | 6/1994 | Lundquist |
| 5,465,716 A | 11/1995 | Avitall |
| 5,487,757 A | 1/1996 | Truckai et al. |
| 2003/0167082 A1 * | 9/2003 | Ollivier et al. ............... 607/126 |

FOREIGN PATENT DOCUMENTS

| EP | 0 347 098 | 12/1989 |
| EP | 0 773 037 | 5/1997 |
| WO | WO 99/56668 | 11/1999 |
| WO | WO 01/78605 | 10/2001 |
| WO | WO 03/002197 | 1/2003 |
| WO | WO 2004/098701 | 11/2004 |

\* cited by examiner

*Primary Examiner* — Gary Jackson
*Assistant Examiner* — Michael Mendoza

(57) ABSTRACT

A steerable stylet for a medical implantable lead has an inner lumen, into which the steerable stylet is insertable for navigating a distal end of the medical implantable lead to the desired location for attachment to tissue. The steerable stylet comprises a wire, a tube and an actuator. By means of the steerable stylet, the distal portion of the lead may be bent in desirable degree and, when the medical implantable lead is bent, the distal portion of the medical implantable lead is pivotal by means of the actuator to which the proximal end of the wire is non-rotatably connected. The tube is connected to the actuator by means of a torque limitation device which, when exceeding a predetermined torque force, will disconnect the torque connection between the tube and the actuator. A method for manufacturing of a steerable stylet for a medical implantable lead includes the step of connecting the stylet tube to the actuator by a torque limiting device as described above.

3 Claims, 5 Drawing Sheets

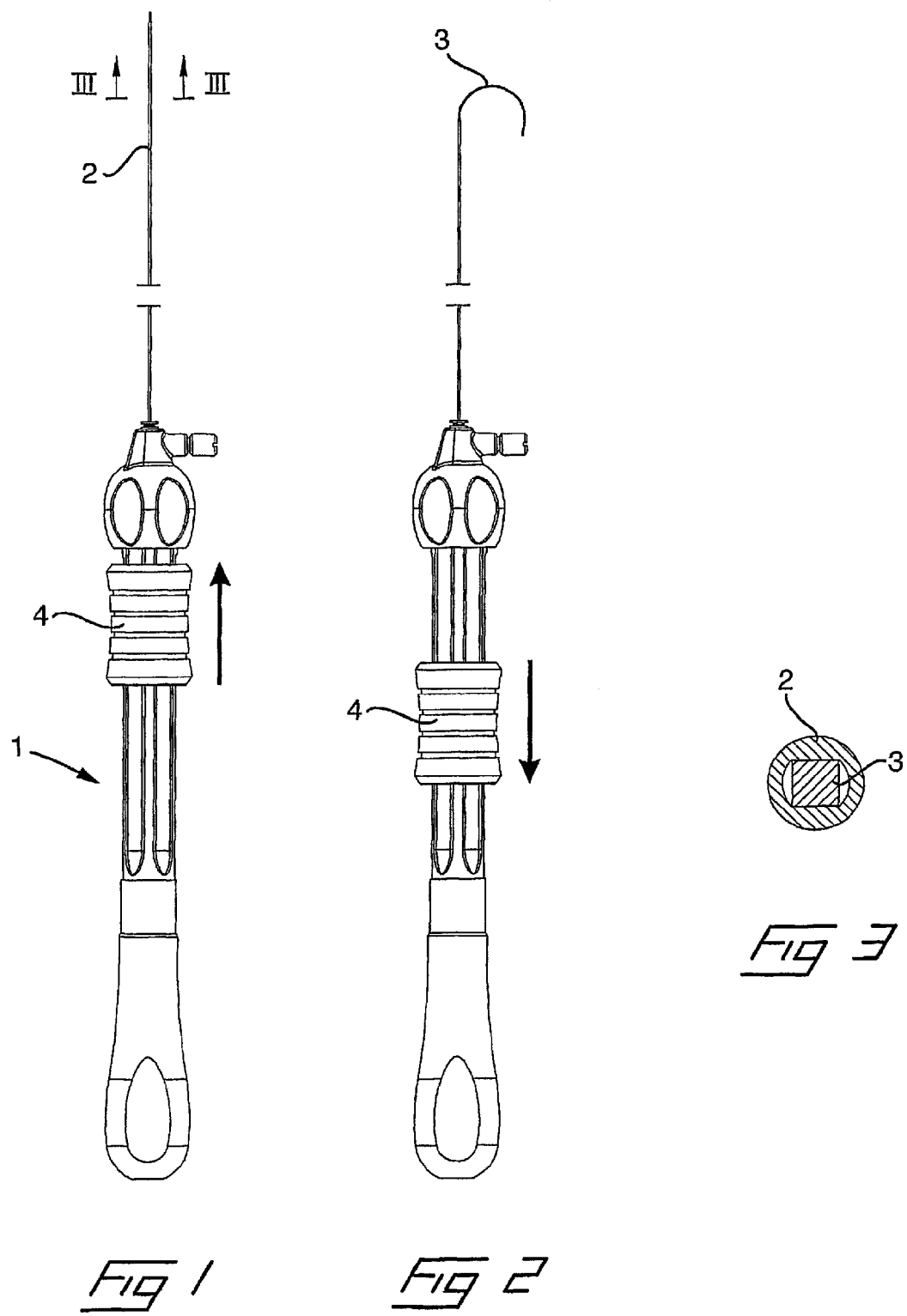

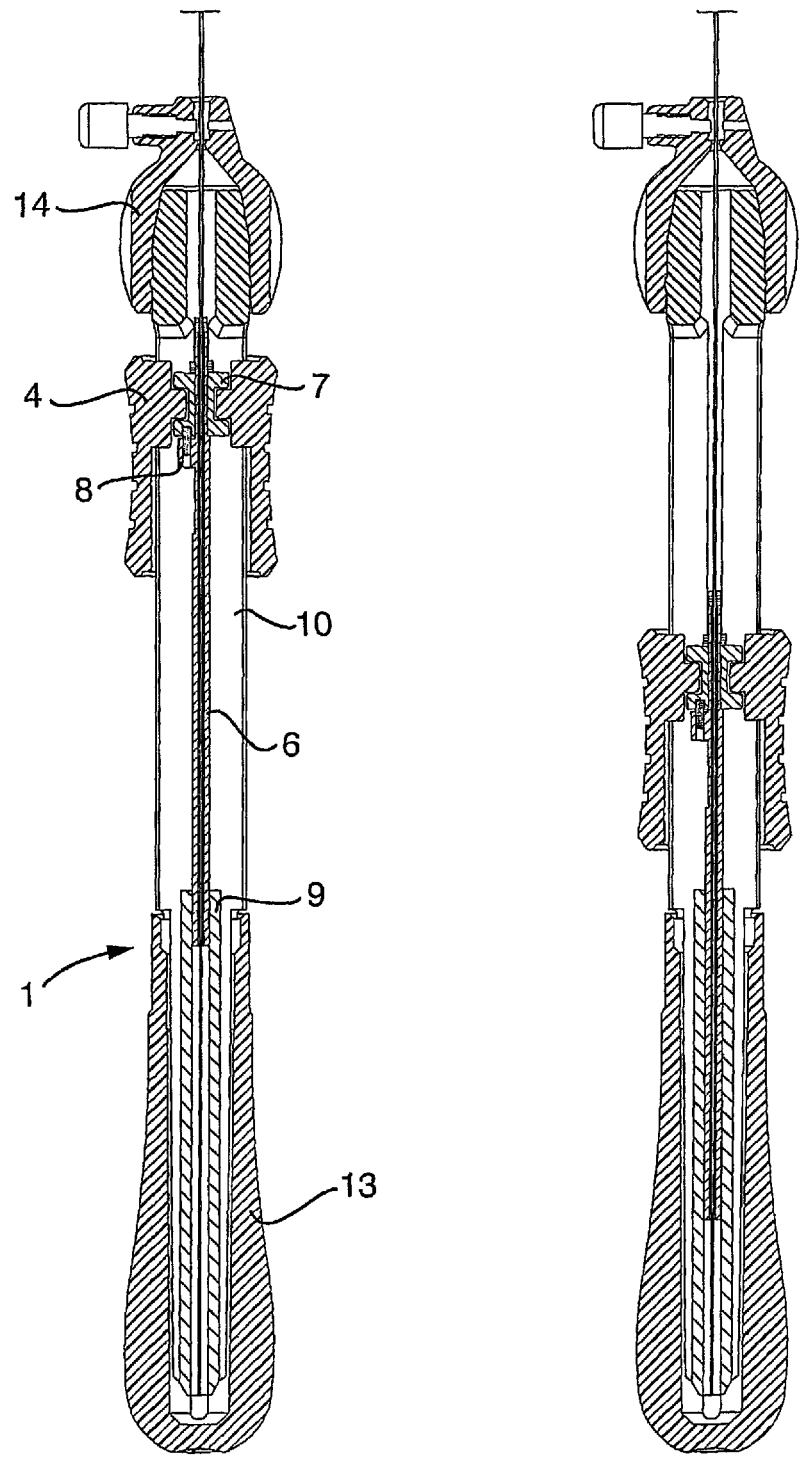

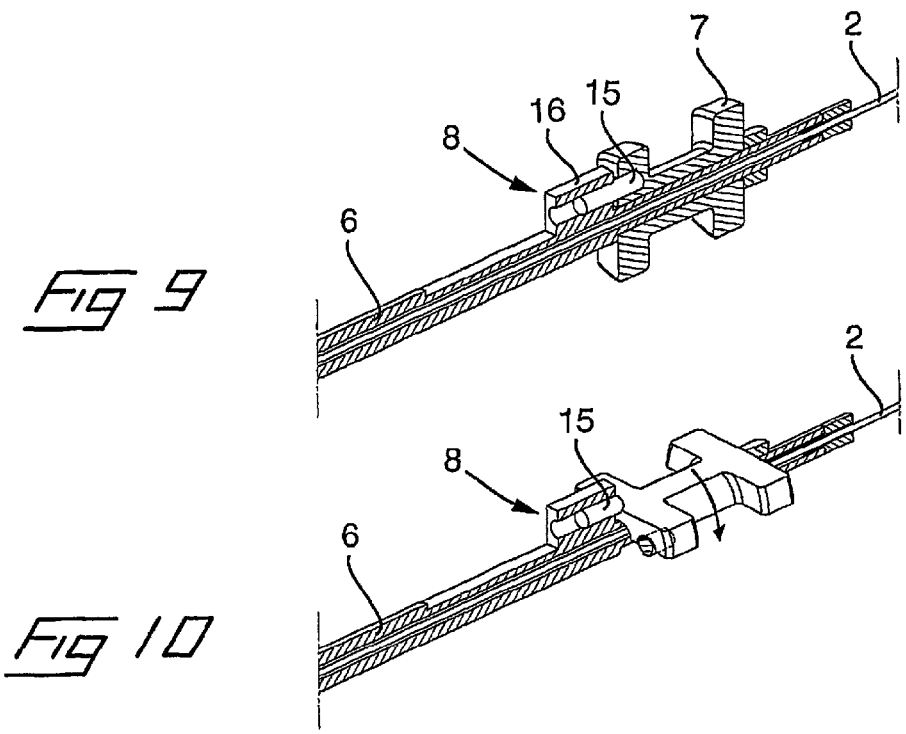
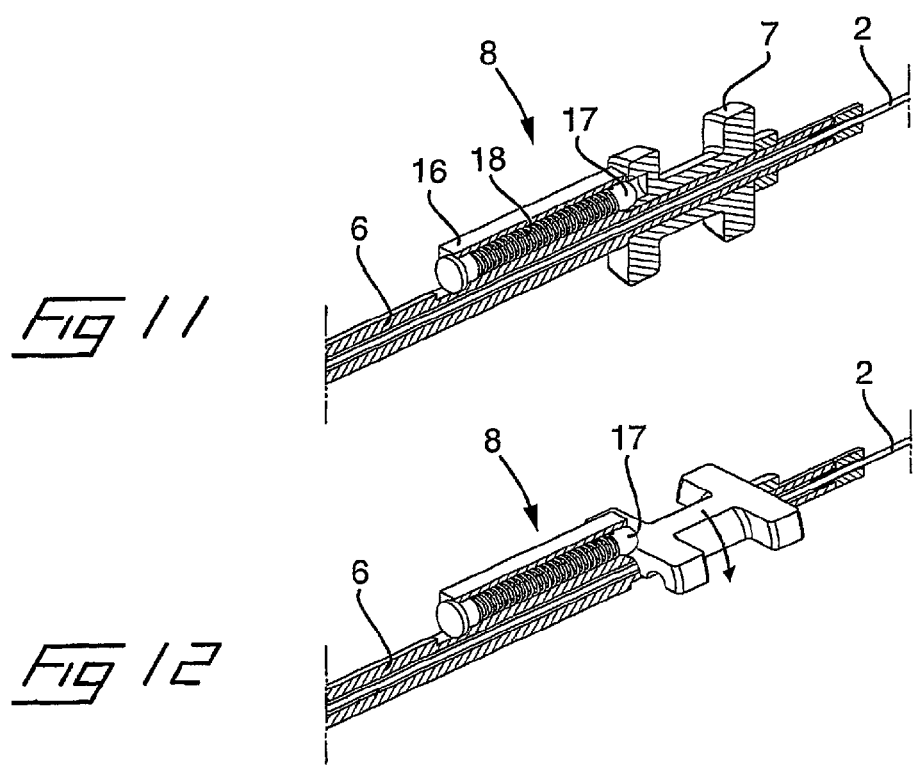

STEERABLE STYLET FOR AN IMPLANTABLE MEDICAL LEAD, AND METHOD FOR MANUFACTURE THEREOF

BACKGROUND OF THE INVENTION

1. Field of the Invention

The invention relates to a steerable stylet for a medical implantable lead of the type having an inner lumen, into which the steerable stylet is insertable for navigating a distal end of the medical implantable lead to the desired location for attachment to tissue, the steerable stylet comprising an elastic tube, a likewise elastic wire, being insertable into the tube, and an actuator in a proximal end for manipulating them in relation to each other, wherein the tube and the wire being arranged such that, when the wire is inserted into the tube, the tube and the wire are non-rotatable in relation to each other and at least the wire is pre-bent in one direction such that a distal portion of the steerable stylet, and hence also the medical implantable lead, may be bent in desirable degree by displacing the tube and the wire in relation to each other such that a portion of the wire protrudes from the distal end of the tube and, when the medical implantable lead is bent, the distal portion of the medical implantable lead is pivotal by means of the actuator to which the proximal end of the wire is non-rotatably connected.

The invention also relates to a method for manufacturing of a steerable stylet for a medical implantable lead.

2. Description of the Prior Art

A steerable stylet of the above kind is known since long time and is used to navigate the distal end portion of a medical implantable lead inside a human or animal body to locate the distal end tip of the lead to a desired position in the tissue. For instance it is common practice to use such a steerable stylet to navigate the distal end tip of a pacemaker lead inside a heart to attach the lead tip to an appropriate position at the heart wall. However, the steerable stylet could also be used to navigate other types of medical implantable leads for monitoring, measuring, controlling or treating arbitrary organs inside the body.

The tube and the wire of the steerable stylet are displaceable in relation to each other. However, the tube and the wire are also unrotatable arranged in relation to each other. This can be accomplished in different ways, but normally it is achieved by that a portion of the inner bore of the tube being non-circular in cross section and the wire being in cross section complementary to the tube bore section such that they can be displaced but not rotated in relation to each other. This portion of the tube and the wire is preferably located in their distal end portions but could also be located on a distance, e.g. 10 to 15 cm, from the distal end. By also manufacturing the tube as well as the wire of an elastic material and pre-bend at least the distal end portion of the wire in one direction or, preferably, pre-bend the distal end portions of both the tube and the wire such that they are pre-bent in opposite directions when assembled together, the tip portion will be satisfactory straight when the ends of the tube and the wire are in an initial position, preferably with their ends coinciding with each other, in which case the straight tube, which has the largest flexural rigidity, will counteract the bending force in the wire, or the bending forces in opposite directions of the tube and the wire will essentially counterbalance each other, whereas the tip portion will bend in one direction when the tube is retracted in relation to the wire, or the wire is advanced in relation to the tube. Since the steerable stylet is positioned inside the lead, which is highly flexible, also the tip portion of the lead will bend in the same direction. The degree of curvature can be regulated by changing the amount of retracting or advancing of the tube and the wire, respectively. With the tip portion in a curved state, it can subsequently be pivoted by rotating the actuator to seek the best possible position for the tip portion. The navigating procedure can be visually monitored by means of e.g. x-ray imaging or magnetic resonance imaging.

In prior art technique, it is common practice to have only the wire unrotatably connected to the actuator, which has to result that only the wire will contribute to the pivoting motion of the lead tip. This is done for security reasons, since if the lead tip should be constrained from pivoting, e.g. due to abutment against tissue or the like, and the steerable stylet is overstressed by excess rotating of the actuator, the steerable stylet will eventually failure by way of the wire most likely snapping off at the attachment point to the actuator. This is harmless since the physician will be aware of the failure and the wire can easily be drawn out from the lead without risking that any part of it will be left in the lead or the body. However, when only the wire is contributing to the pivotal movement, the movement will be difficult to control since the wire is so weak and has a low torsional stiffness. Hence, it is difficult to navigate the lead tip to the desired position. This problem could be overcome by attaching also the tube non-rotatably to the actuator. However, this could be risky since then overstressing of the steerable stylet could lead to that the wire, which most likely will failure before the tube since it is much weaker, could snap off at a region at its distal end portion since in this case the strains will be as largest in this region. A failure in this region will be more dangerous since here the failure is harder to recognize and pieces from the wire—or the tube—can be left in the lead or the body.

SUMMARY OF THE INVENTION

An object of the invention is to improve prior art steerable stylets of the related art. More precisely, it is an object of the invention to improve the controllability of the steerable stylet without jeopardizing the security for the patient.

The invention also relates to a method for manufacturing of a steerable stylet for a medical implantable lead, having essentially the same object as above. At least this object is achieved by a method according to claim 5.

The above object is achieved in accordance with the invention by connecting the tube to the actuator by means of a torque limiting device, which allows transferring of a limited torque from the actuator to the tube but which, upon exceeding this torque limit or threshold value, will release the rotation preventing connection of the tube to the actuator and make it rotatable in relation to the actuator. In this way the tube and the wire may interact to pivot the distal end of the steerable stylet and the lead, which give increased controllability during navigation. If, however, the distal end of the lead should be stuck, or rotation is obstructed in any other way, but the rotation of the actuator is continued until the steerable stylet is overstressed, the torque coupling between the tube and the actuator is eventually exceeded such that the torque limiting device will release and the torque is transferred to the lead tip by means of the wire only. Should the wire subsequently snap off during navigating of the lead due to overstress, this will occur at the proximal end in the vicinity of the actuator, which is not critical, as is mentioned before. Accordingly, the torque limiting device should be designed such that the torque connection will be released before the ultimate tensile strength for the wire is reached.

Within this general idea, the invention may be implemented in many different ways. In the hereinafter given detailed description of preferred embodiments, the invention is shown in two different embodiments. In both embodiments the tube is provided with a thickened, shaft portion on which a carrier element is mounted rotatably but undisplaceably in the longitudinal direction. The carrier element is in engagement with an outer tube shaped actuator handle and an actuator slide, by means of which the shaft portion of the tube may be displaced in relation to a likewise thickened shaft portion of the wire, which is in un-rotatable engagement with the actuator handle. The torque limitation device is in both of the embodiments accomplished by connecting the carrier element un-rotatably with a bracket-like support on the tube shaft. The connection is in one of the embodiments in form of a spring-loaded ball, which engages a recess in the carrier element, and in the other embodiment by means of a break-pin. When exceeding the predetermined torque limit, the ball will disengage from the recess and the break-pin will break, respectively, which will release the carrier element from the bracket support and hence from the torque connection with the tube.

One advantage with a torque limitation device in form of a spring loaded ball is that it is reusable such that when it once has reached the torque limit, the ball will disengage from the recess and the tube will rotate one turn and then go into engagement again. In the break pin embodiment, on the other hand, the break pin will break when reaching the torque limit and thereafter the torque connection can not be established any more, unless the break pin is replaced with a new one. However, it is to be understood that these embodiments are only exemplary and that the specific configuration of the invention may be performed in many different ways within the scope of the claims.

BRIEF DESCRIPTION OF THE DRAWINGS

FIG. 1 shows and embodiment of a steerable stylet according to the invention with the distal end portion of the stylet in a straight condition.

FIG. 2 shows the stylet of FIG. 1 with the distal end portion in a curved condition.

FIG. 3 is an enlarged cross section of the stylet of FIG. 1 along line III-III.

FIG. 7 is a longitudinal section of an actuator handle of the steerable stylet according to the invention, in an initial position when the stylet is straight.

FIG. 8 is a longitudinal section of the actuator handle of FIG. 7, in a position when the distal end portion of the stylet is curved.

FIG. 9 is an enlarged longitudinal section, in perspective, of the arrangement of a torque limiting device according to a first embodiment of the invention, in an engaged state.

FIG. 10 is a section according to FIG. 9 with the torque limiting device released.

FIG. 11 is an enlarged longitudinal section, in perspective, of the arrangement of a torque limiting device according to a second embodiment of the invention, in an engaged state.

FIG. 12 is a section according to FIG. 11, with the torque limiting device released.

DESCRIPTION OF THE PREFERRED EMBODIMENTS

Reference is first made to FIGS. 1-2 in which are depicted a steerable stylet comprising an actuator in form of a handle 1, which is connected to a stylet comprised of a thin, elastic tube 2 having an inner bore into which a likewise thin and elastic wire 3 is insertable, the distal end portion of which is visible in FIG. 2. The tube 2 and the wire 3 are displaceable in relation to each other but they are unrotatable arranged in relation to each other in the distal end portion. The unrotatable feature is achieved by, as is shown in a cross section through the distal end portion of the tube and wire in FIG. 3, that the inner bore of the tube 2 is formed with a flattened cross section as well as the cross section of the wire 3 being flattened. Moreover, the distal end portions of the tube and the wire are pre-bent and assembled such that the pre-bent portions are curved in different directions. This has to effect that when the tube and the wire are located with their respective distal ends essentially coinciding, as in FIG. 1, the stylet will assume an essentially straight form. From this position the tube 2 can be retracted, as is shown in FIG. 2, by means of retracting an actuator slide 4 on the handle. This has to effect that the distal portion of the wire 3, will protrude a distance from the distal end of the tube 2 and will therefore assume a curved form due to its pre-bent shape.

Figure 4:
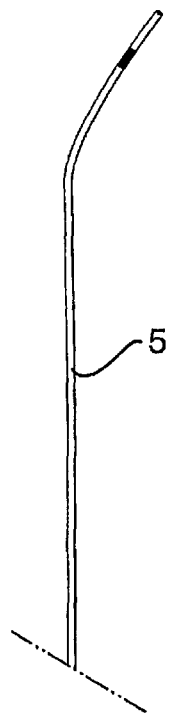
FIG. 4 is a sectional view of medical implantable lead.

In FIG. 4 is depicted a medical implantable lead 5, which in this case is a pacemaker lead adapted to be attached to tissue inside a heart. The lead 5 is highly flexible and has an inner lumen. To accomplish attachment to tissue inside the heart, the lead is provided with a helix, not shown in the drawings, which is extendable out from the distal end of the lead to be screwed into the tissue.

Figure 5:
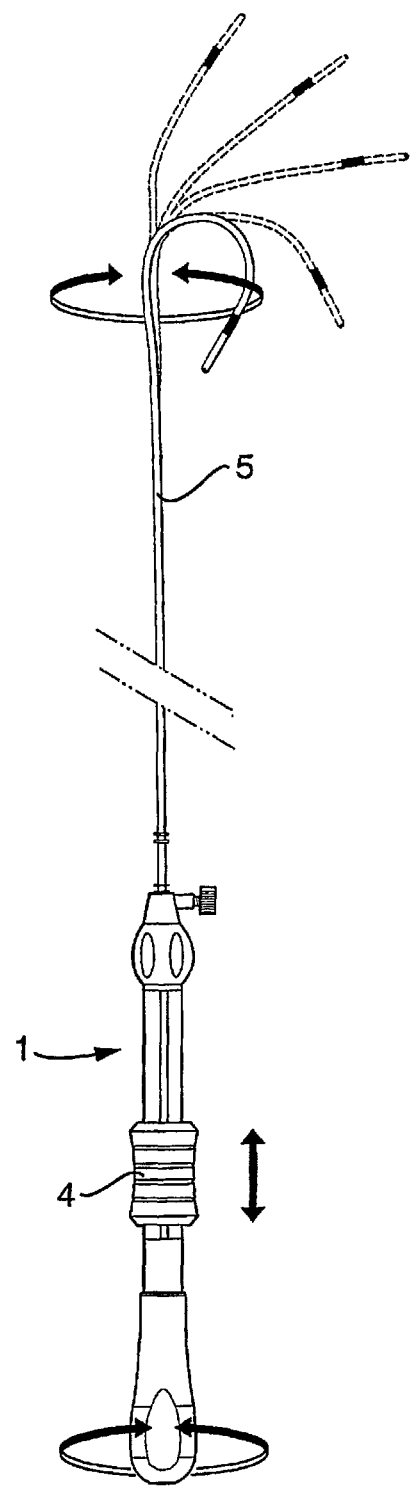
FIG. 5 shows curving and pivoting of the distal end of the lead by means of the steerable stylet in accordance with the invention.

To enable navigation of the distal end of the lead to a suitable location inside the heart for attachment, the stylet 2, 3 of the steerable stylet in FIGS. 1 and 2, is insertable into the bore of the lead. By means of the steerable stylet, the distal portion of the lead can be curved in a desired degree, as is illustrated in FIG. 5, by displacing the actuator slide 4. By also rotating the actuator handle 1, the distal, curved portion of the lead can be pivoted until a desired location of the distal lead end has been reached. The navigation of the lead can be monitored by means of for example x-ray imaging.

Figure 6:
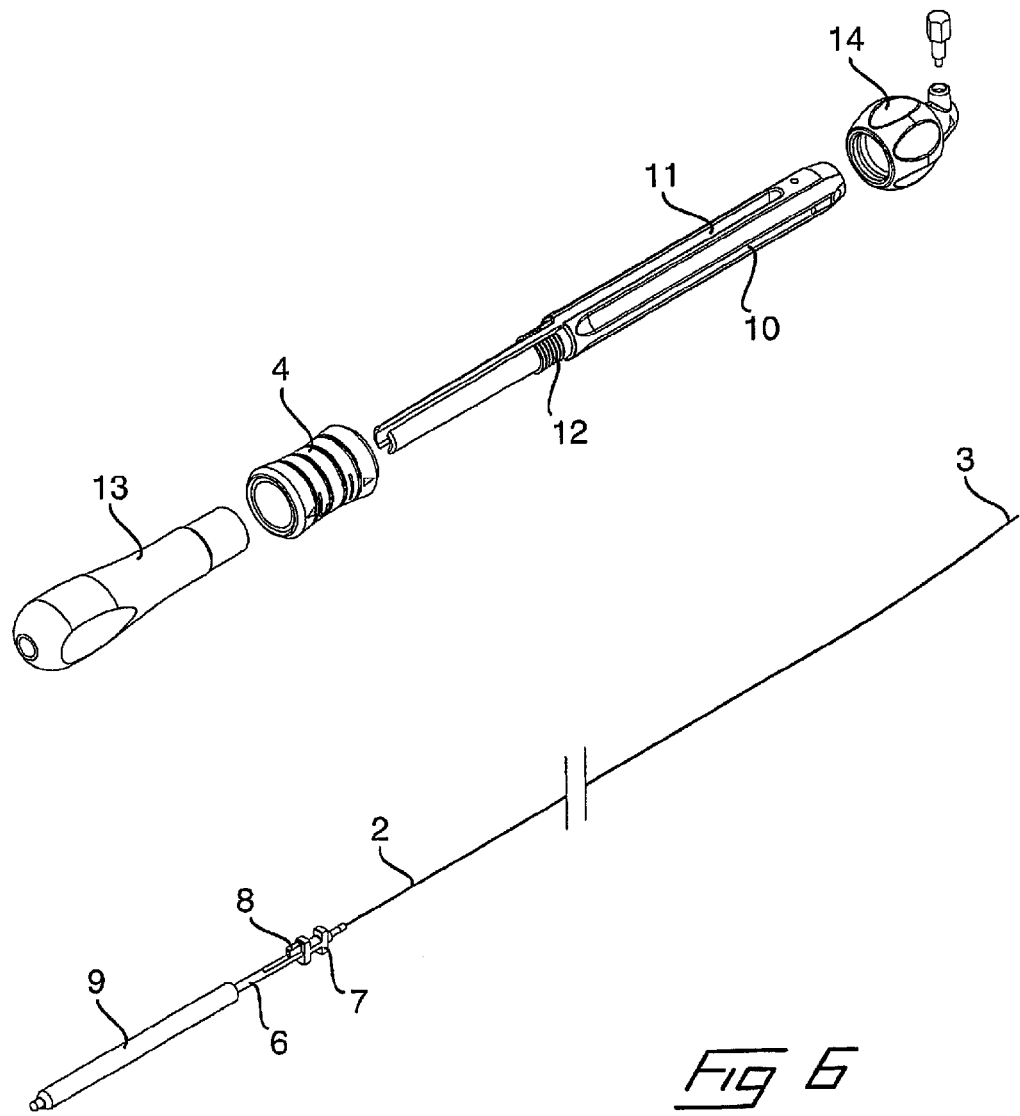
FIG. 6 is an explodable view of a steerable stylet according to the invention.

Now reference is made to FIG. 6, in which an exploded perspective view of the steerable stylet is shown. From the drawing can be seen the tube 2 and the wire 3 of the stylet. In a proximal portion of the stylet, a part which in an assembled state is covered by the actuator handle 1, the tube is formed with a thickened shaft portion 6 on which a carrier element 7 is mounted rotatably but un-displaceably in the longitudinal direction. Rigidly attached to the tube shaft 6 is also a torque limitation device 8, which will be discussed more in detail below. Also the wire 3, of which the distal portion is visible in the drawing, is provided with a thickened shaft portion 9 in its proximal end. The tube shaft 6 and the wire shaft 9 can be displaced in relation to each other, namely such that the tube shaft 6 is telescopic displaceable into an inner bore in the wire shaft 9.

The actuator handle 1 has an elongated handle shaft 10 having an elongated slot 11 and a threaded portion 12. When assembling the steerable stylet, the stylet is inserted through a hole in the distal end of the handle shaft 10, such that the tube shaft 6, the wire shaft 9 as well as the carrier element 7 and the torque limitation device 8 will be located in the slot 11 of the handle shaft 10. The actuator slide 4 is ring shaped and is adapted to be thread on the handle shaft 10 and on the inside be in engagement with the carrier element 7. From the proximal end of the handle, an end piece 13 is screwed onto the threads 12 on the handle shaft 10. By means of an actuator handle formed in this way, the wire shaft 9 will be clamped within the handle shaft 10 by means of the end piece 13, such that the wire and the actuator handle will be held unrotatably in relation to each other. The carrier element 7 will be slidable within the slot 11 by means of the actuator slide 4, such that the tube 2 can be retracted by the tube shaft 6 being displaceable into the wire shaft 9. However, this will not restrict the rotation of the tube 2 in relation to the actuator shaft, since the carrier element 7 is rotatable in relation to the tube shaft 6. According to the invention, the rotation of the tube 2 and the tube shaft 6 is restricted by the torque limitation device 8 due to the fact that the torque limitation device is rigidly attached to the tube shaft 6 and is connected to the carrier element 7. This will be described in more detail below. The actuator handle also includes a helix rotator 14, which can be attached to a connector pin in the proximal end of the lead, which by some suitable means, e.g. a rotatable coil in the lead, is in connection with the helix and can accomplish extension of the helix from the distal end of the lead by rotation of the helix rotator 14. However, this kind of helix arrangement is not a part of the present invention but is well known in the art and will therefore not be described any further herein.

The actuator handle 1 is shown in longitudinal sections in an assembled state in FIGS. 7 and 8, with the actuator slide 4 in an advanced initial position in FIG. 7, when the stylet is essentially straight, and in a retracted position in FIG. 8, when the stylet is curved.

In FIG. 9 is shown a perspective view in an enlarged scale, of the tube 2, the tube shaft 6, the carrier element 7 and a first embodiment of the torque limitation device 8. In this embodiment the torque limitation device comprises a break pin 15, which is held by a bracket support 16 and is extended into a recess in the carrier element 7. As is mentioned before, the carrier element is rotatable around the tube shaft 6 but as long as the break pin 15 connects the carrier element and the bracket support 16, which is rigidly connected to the tube shaft 6, any rotationally movement of the actuator handle 1 will be transmitted via the carrier element 7, the brake pin 15, the bracket support 16 and the tube shaft 6 to the tube 2 such that it can participate in pivoting the distal end of the stylet and the lead 5.

In FIG. 10 is illustrated a case when the torque limit for the torque limitation device 8 has been exceeded and the break pin 15 has been broken. Now the tube shaft 6 and the tube 2 are free to rotate independently of the actuator shaft 1 and the tube 2 will accordingly not participate in the pivoting of the distal, curved end of the lead. Instead any such pivoting has to be carried out by the wire 3 only.

In FIG. 11 is shown a corresponding perspective view in an enlarged scale, of a second embodiment of the torque limitation device 8. In this embodiment the torque limitation device comprises a ball 17, which is held by the bracket support 16 and is forced towards a recess in the carrier element 7 by means of a spring 18. As long as the ball 17 is in engagement with the recess in the carrier element 7, any rotationally movement of the actuator handle 1 will, in a corresponding way as the embodiment in FIGS. 9 and 10, be transmitted via the carrier element 7, the ball 17, the bracket support 16 and the tube shaft 6 to the tube 2 such that the tube can participate in pivoting the distal end of the stylet and the lead 5.

In FIG. 12 is illustrated a corresponding case when the torque limit for the torque limitation device 8 has been exceeded and the ball 17 has been forced out of engagement of the recess in the carrier element. Now the tube shaft 6 and the tube 2 are free to rotate independently of the actuator shaft 1 and the tube 2 will accordingly not participate in the pivoting of the distal, curved end of the lead. Instead any such pivoting has to be carried out by the wire 3 only.

Although modifications and changes may be suggested by those skilled in the art, it is the intention of the inventor to embody within the patent warranted heron all changes and modifications as reasonably and properly come within the scope of his contribution to the art.

I claim as my invention:

1. A steerable stylet for a medical implantable lead having an inner lumen into which the steerable stylet is insertable for navigating a distal end of the medical implantable lead to a desired location for attachment to tissue, the steerable stylet comprising:

an elastic tube;

an elastic wire being insertable into the tube; and an actuator in a proximal end to manipulate the elastic tube and elastic wire in relation to each other, wherein the tube and the wire are arranged such that, when the wire is inserted into the tube, the tube and the wire are non-rotatable arranged in relation to each other and at least the wire is pre-bent in one direction such that a distal portion of the steerable stylet, as well as the medical implantable lead, may be bent in desirable degree by displacing the tube and the wire in relation to each other such that a pre-bent portion of the wire protrudes from the distal end of the tube and, when the medical implantable lead is bent, the distal portion of the medical implantable lead is pivotal by means of the actuator to which the proximal end of the wire is non-rotatably connected, the tube being connected to the actuator by a torque limitation device which, when exceeding a predetermined torque force, disconnects the torque connection between the tube and the actuator;

wherein the torque limitation device comprises a bracket support, which is rigidly connected to a tube shaft, which is rigidly connected to the tube, and a carrier element, which is rotatably but undisplaceably connected to the tube shaft and is unrotatably connected to an actuator, and wherein the bracket support and the carrier element are connected by a device for transmitting a limited torque.

2. A steerable stylet according to claim 1, wherein the device for transmitting a limited torque is a break pin.

3. A steerable stylet according to claim 1, wherein the device for transmitting a limited torque is a spring-loaded ball.

\* \* \* \* \*